United States Patent [19]
Yamamoto

[11] Patent Number: 5,620,846
[45] Date of Patent: Apr. 15, 1997

[54] DIAGNOSTIC AND PROGNOSTIC INDICES FOR CANCER AND AIDS

[76] Inventor: Nobuto Yamamoto, 1040 66th Ave., Philadelphia, Pa. 19126

[21] Appl. No.: 478,121

[22] Filed: Jun. 7, 1995

[51] Int. Cl.$^6$ ................................................ C12Q 1/70
[52] U.S. Cl. .................... 435/5; 435/18; 435/34; 435/974; 436/501
[58] Field of Search ............... 435/4, 5, 18, 34, 435/974; 436/501

[56] References Cited

PUBLICATIONS

Yagi et al, "Glycosidases of Ehrlich Ascites Tumor Cells and Ascitic Fluid–Purfication and Substrate Specificity of α–N–Acetylgalactosaminidase and α–Galactosidase: Comparison with Coffee Bean α–Galactosidase", *Archives of Biochemistry and Biophysics*, vol. 280, No. 1 (Jul. 1990), pp. 61–67.

Yamamoto et al, "Deglycosylation of Serum Vitamin D3–Binding Protein Leads to Immunosuppression in Cancer Patients", *Cancer Research*, vol. 56, No. 12(1996 Jun. 15), pp. 2827–2831.

Yamamoto et al, "Structural Modification of Serum Vitamin D3–Binding Protein and Immunosuppression in AIDS Patients", *AIDS Research in Human Retroviruses*, vol. 11, No. 11(1995 Nov.), pp. 1373–1378.

Genomics, vol. 16, issued 1993, Witke et al., "Complet Structure of the Human Gc Gene: Differences and Similarities Between Members of the Albumin Gene Family", pp.751–754 see entire document.

Biochimica et Biophysica Acta, vol. 1216, issued 1993, Braun et al., "Sequence and Organization of the Human Vitamin D Binding Protein Gene", pp. 385–394, see entire document.

Proceedings of the National Academy of Science, U.S.A., vol. 82, issue Dec. 1985, Yang et al. "Human Group–Specifi Component (Gc) is a Member of the Albumin Family", pp. 7994–7998, see entire document.

Biochemica Et Biophysica Acta, vol. 871, issued 1986 Schoentgen et al., "Complete Amino Acids Sequence of Huma Vitamin D–Binding Protein (Group–Specific Component): Evidence of a Three–fold Internal Homology as a Serum Albumin an alpha–Fetoprotein", pp. 189–198, see entire document.

Ngwenya, B.Z., and Yamamoto, N. 1985. Activation of peritoneal macrophages by Iysophosphatidylcholine. Biochem. Biophys. Acta 839:9–15.

Ngwenya, B.Z., and Yamamoto, N. 1990. Contribution of lysophosphatidyl–choline treated nonadherent cells to mechanism of macrophage stimulation. Proc. Soc. Exp. Biol. Med. 193:118–124.

Yagi, F., Eckhardt, A. E. and Goldstein I. J. 1990. Glycosidases of Ehrlich ascites tumor cells and ascitic fluid–purification and substrate specificity inidase and α–galactosidase: Comparison with coffee bean α–galactosidase. Arch. Biochem. Biophys. 280:61–67.

Yamamoto, N. and Homman, S. 1991. Vitamin $D_3$ binding protein (group–specific component, Gc) is a precursor for the macrophage activating signal from sophosphatidylcholine–treated lymphocytes. Proc. Natl. Acad. Sci. USA. 88:8539–8543.

Yamamoto, N. and Kumashiro, R. 1993. Conversion of vitamin $D_3$ binding protein (Group–specific component) to a macrophage activating factor by stepwise action of β–galactosidase of B cells and sialidase of T cells. J. Imunol. 151:2794–2902.

Homma, S., Yamamoto, M. and Yamamoto, N. 1993. Vitamin D binding protein (group–specific component, Gc) is the sole serum protein required for macrophage activation after treatment of peritoneal cells with lysophosphatidylcholine. Immunol. Cell Biol. 71:249–257.

Yamamoto, N., Kumashiro, R., Yamamoto, M., Willett, N.P. and Lindsay, D. D. 1993. Regulation of inflammation–primed activation of macrophages by two serum factors, vitamin $D_3$–binding protein and albumin. Inf. Imm. 61:5388–5391.

Yamamoto, N., Willett, N. P. and Lindsay, D. D. 1994. Participation of serum proteins in the inflammation–primed activation of macrophages. Inflammation. 18:311–322.

Naraparaju, V. R. and Yamamoto, N. 1994. Roles of β–galactosidase of B lymphocytes and sialidase of T lymphocytes in infammation–primed activation of macrophages. *Immunol. Lett.* 43:143–148.

*Primary Examiner*—Christine M. Nucker
*Assistant Examiner*—Jeffrey Stucker
*Attorney, Agent, or Firm*—Caesar, Rivise, Bernstein, Cohen & Pokotilow, Ltd.

[57] ABSTRACT

Cancerous cells and HIV-infected cells secrete α-N-acetylgalactosaminidase into the blood stream, resulting in deglycosylation of serum Gc protein. This inactivates the MAF precursor activity of Gc protein, leading to immunosuppression. Thus, both α-N-acetylgalactosaminidase activity and MAF precursor activity of Gc protein in patient blood stream can serve as diagnostic and prognostic indices.

In one embodiment is disclosed a process for determining macrophage activating factor precursor activity in plasma or serum of a person suspected of having cancer or HIV, comprising the step of quantifying in the plasma or serum an amount of vitamin $D_3$-binding protein. The determination of the macrophage activating factor precursor activity provides an indication of the patient's capability to activate its own monocytes/macrophages.

In another embodiment is disclosed a process for determining macrophage activating factor precursor activity in plasma or serum of a person suspected of having cancer or HIV comprising the step of quantifying in the plasma or serum an amount of α-N-acetylgalactosaminidase activity. Determining the α-N-acetylgalactosaminidase activity in the plasma or serum provides an indication of a quantity of malignant cells (or HIV) in the plasma or serum.

6 Claims, 1 Drawing Sheet

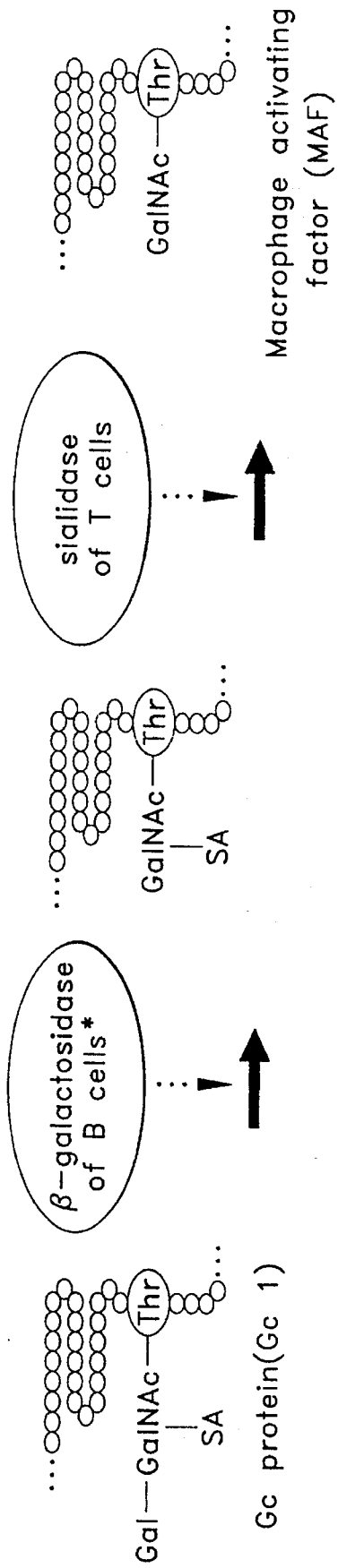
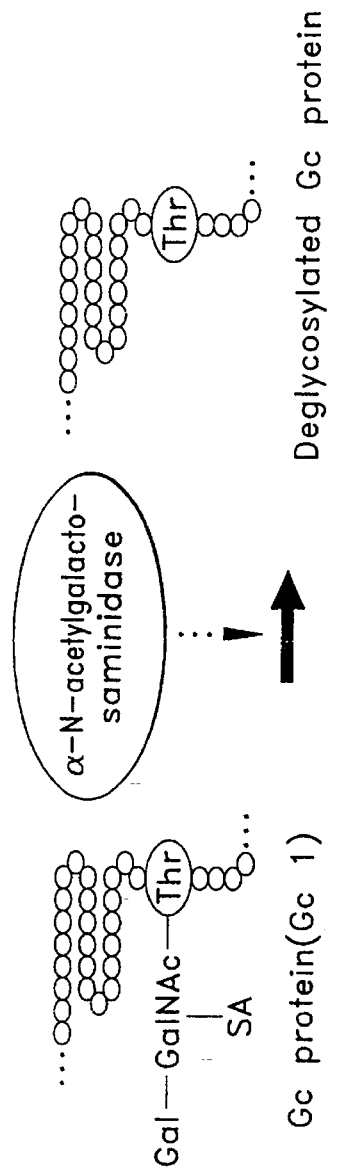
FIG. 1A
FIG. 1B

DIAGNOSTIC AND PROGNOSTIC INDICES FOR CANCER AND AIDS

FIELD OF THE INVENTION

This invention relates to methods to detect immunosuppression in cancer and AIDS patients, particular to the absence or reduced precursor activity for macrophage activating factor due to the presence of a serum glycosidase derived from these diseases.

BACKGROUND OF THE INVENTION

A. Immunosuppression Resulting from Loss of MAF Precursor Activity

Inflammation results in activation of macrophages. Cellular membrane damage and the inflammatory process result in the release of lysophospholipids. Administration into mice of small doses (5–20 μg/mouse) of lysophosphatidylcholine (lyso-Pc) and other lysophospholipids induced a greatly enhanced phagocytic and superoxide generating capacity of macrophages (Ngwenya and Yamamoto, *Proc. Soc. Exp. Biol. Med.* 193:118, 1990; Yamamoto et al., *Inf. Imm.* 61:5388, 1993; Yamamoto et al., *Inflammation.* 18:311, 1994). This macrophage activation requires participation of B cells and T lymphocytes and a serum vitamin D binding protein (DBP; human DBP is known as group specific components or Gc). Activation of mouse peritoneal macrophages by lyso-Pc requires modification of the Gc protein by stepwise association with β-galactosidase of lyso-Pc-treated B cells and sialidase of T cells, to generate the macrophage activating factor (MAF), a protein with N-acetylgalactosamine as the remaining sugar moiety (FIG. 1a) (Yamamoto et al., *Proc. Natl. Acad. Sci. USA.* 88:8539, 1991; Yamamoto et al., *J. Immunol.* 151:2794, 1993). Thus, Gc protein is a precursor for MAF. Incubation of Gc protein with immobilized β-galactosidase and sialidase generates a remarkably high titered MAF (GcMAF) (Yamamoto et al., *Proc. Natl. Acad. Sci. USA.* 88:8539, 1991; Yamamoto et al., *J. Immunol.* 151:2794, 1993; Naraparaju and Yamamoto, *Immunol. Lett.* 43:143, 1994; U.S. Pat. No. 5,177,002). Administration of a minute amount (10 pg/mouse; 100 ng/human) of GcMAF resulted in a greatly enhanced phagocytic capacity of macrophages. When peripheral blood monocytes/macrophages of 175 cancer patients bearing various types of cancer were treated in vitro with 100 pg GcMAF/ml, monocytes/macrophages (phagocytes) of all cancer patients were activated for phagocytic and superoxide generating capacity. This observation indicates that patient phagocytes are capable of being activated. However, the MAF precursor activity of plasma Gc protein was severely reduced in approximately one third of the cancer patient population. Loss of the MAF precursor activity prevents generation of MAF. Therefore, macrophage activation cannot develop in certain cancer patients. Since macrophage activation is the first step in immune development cascade, such cancer patients become immunosuppressed. This may explain at least in party why cancer patients die with overwhelming infections. About one third of the patients had moderately reduced MAF precursor activities while the remaining one third of the cancer patients had MAF precursor activities similar to those of healthy humans. Lost or reduced precursor activity of Gc protein was found to be due to deglycosylation of plasma Gc protein by α-N-acetylgalactosaminidase detected in a cancer patient's blood stream. Deglycosylated Gc protein cannot be converted to MAF (FIG. 1b). The source of the α-N-acetylgalactosaminidase appeared to be cancerous cells. Radiation therapy of cancerous lesions decreased plasma α-N-acetylgalactosaminidase activity with concomitant increase of precursor activity. This implies that radiation therapy decreases the number of cancerous cells capable of secreting α-N-acetylgalactosaminidase. Thus, plasma α-N-acetylgalactosaminidase activity has an inverse correlation with the MAF precursor activity of Gc protein. Both α-N-acetylgalactosaminidase activity and MAF precursor activity of Gc protein in a patient's blood stream can serve as diagnostic and prognostic indices.

Similarly, when peripheral blood monocytes/macrophages of 65 HIV-infected/AIDS patients were treated in vitro with 100 pg GcMAF/ml, the monocytes/macrophages of all patients were activated for phagocytic and superoxide generating capacity. However, the MAF precursor activity of plasma Gc protein was severely reduced in about 1/10 of the HIV-infected patient population and approximately 25% of AIDS patients. These patients' plasma Gc protein is deglycosylated by α-N-acetylgalactosaminidase detected in HIV-infected patients. HIV-infected cells appeared to secrete α-N-acetylgalactosaminidase. Thus, α-N-acetylgalactosaminidase activity and MAF precursor activity of Gc protein in the patient's blood stream can serve as diagnostic and prognostic indices.

In my prior two U.S. Pat. Nos. 5,177,001 and 5,177,002, the entire disclosures of which are incorporated by reference herein, as are my above cited journal articles, is disclosed various macrophage activating factors, processes for preparing them as well as methods of inducing macrophage activation in a person in need of such activation.

B. The Origin of α-N-acetylgalactosaminidase

Loss of the precursor activity was found to be due to deglycosylation of plasma Gc protein by α-N-acetylgalactosaminidase detected in the patient blood stream. The source of the enzyme appeared to be cancerous cells. Ehrlich ascites tumor cells contain a large amount of β-N-acetylglucosaminidase and a very small amount of α-N-acetylgalactosaminidase (Yagi et al., *Arch Biochem Biophys.* 280:61, 1990).

My data has indicated that both β-N-acetylglucosaminidase and α-N-acetylgalactosaminidase were detected in tumor tissue homogenates as represented by enzyme activities (about 41.5 and 32.1 nmole/mg/min, respectively) of a lung tumor tissue. Similar results were also observed with eleven different tumor tissues including 4 lung, 3 breast, 3 colon and 1 cervix tumors, though the α-N-acetylgalactosaminidase activity varied from 5.9 to 50.8 nmoles/mg/min. Radiation therapy of cancerous lesions decreased plasma α-N-acetylgalactosaminidase activity with concomitant increase of precursor activity. This implies that radiation therapy decreases the number of cancerous cells capable of secreting α-N-acetylgalactosaminidase.

Similarly HIV-infected patients carry α-N-acetylgalactosaminidase activity in their blood stream. HIV-envelope protein was found to contain α-N-acetylgalactosaminidase activity. HIV-infected cells can secrete this enzyme in to blood stream, resulting in deglycosylation of Gc protein. This would cause immunosuppression in HIV-infected/AIDS patients.

Thus, both α-N-acetylgalactosaminidase activity and MAF precursor activity of Gc protein in patient blood stream can serve as excellent diagnostic and prognostic indices.

SUMMARY OF ASSAY PROCEDURES FOR PLASMA α-N-ACETYLGALACTOSAMINIDASE ACTIVITY AND MAF PRECURSOR ACTIVITY OF Gc PROTEIN:

1. Precursor activity of vitamin D-binding protein (Gc protein) in patient plasma/serum for the macrophage activating factor.

Assay procedure for precursor activity of serum (Gc protein) of cancer patient and HIV-infected/AIDS patients.

Step I. Lysophosphatidylcholine (Lyso-Pc)-treatment of mouse peritoneal cells (mixture of lymphocytes and macrophages):

Lyso-Pc (1 μg/ml)+mouse peritoneal cells
{30 min incubation at 37° C. }→{washed with PBS}

Step II. Lyso-Pc-treated peritoneal cells+gammaglobulin-depleted patient plasma/serum (0.1%)
{3 hr cultivation at 37° C.}→macrophage activation assay.
{assay of superoxide generation}

Precursor activity estimation: nanomoles of superoxide produced/min/$10^6$ cells with patient plasma/serum compared with that of healthy human plasma/serum.

2. Detection of α-N-acetylgalactosaminidase in blood stream of cancer and HIV-infected/AIDS patients.

Detection procedure for deglycosylating enzyme of serum Gc protein, α-N-acetylgalactosaminidase, in cancer patient and HIV-infected/AIDS patient blood stream.

Step I. Stepwise 30/70% ammonium sulfate precipitation of patient plasma/serum:

Patient plasma/sera (1 ml)+30% and 70% saturated ammonium sulfate 70% precipitate→dissolved in 50 mM citrate phosphate buffer (pH 6.0)→dialyzed against the same buffer at 4° C. for overnight.

Step II. Enzyme assay of α-N-acetylgalactosaminidase

Reaction mixture: 100 μl of the dialyzed sample+1.0 ml of 50 mM citrate phosphate buffer (pH 6.0) containing 5 μmoles of p-nitrophenyl N-acetyl-α-D-galactosaminide as substrate.

Incubation time: 60 min, terminated by adding 200 μl of 0.5M $Na_2CO_3$.

Activity measurement: absorbance of amount of released p-nitrophenol at 420 nm and expressed as nmoles/min.

DESCRIPTION OF THE METHODS

1. Precursor activity of serum Gc protein of cancer and HIV-infected/AIDS patients.

To determine precursor activity of Gc protein, mouse peritoneal cells (mixture of lymphocytes and macrophages) will be incubated with 1 μg lysophosphatidylcholine (lyso-Pc)/ml in 0.1% egg albumin supplemented medium RPMI-1640 (EA medium) at 37° C. for 30 min. The lyso-Pc-treated peritoneal cells will be washed with PBS and cultured for 3 h at 37° C. in EA medium supplemented with gammaglobulin-depleted* patient plasma/serum (0.1%) and assayed for superoxide generation of the macrophages. Loss or decrease of precursor activity of serum Gc protein results in lack or reduction of superoxide generation. Thus, the precursor activity is expressed by amounts of superoxide generated (nmoles of superoxide produced/min/$10^6$ cells).

*Note: Since adult human serum appears to contain interspecific lymphocyte cytotoxic antibodies against mouse lymphocytes (Homma et al., Immunol. Cell Biol. 71:249, 1993), IgG fraction should be depleted using Protein A Sepharose Cl-4B beads.

2. Assay procedure for α-N-acetylgalactosaminidase.

Plasma/serum (1 ml) of a healthy human and patients will be precipitated with 70% saturated ammonium sulfate. The ammonium sulfate precipitate will be dissolved in 50 mM citrate phosphate buffer (pH 6.0) and dialyzed against the same buffer at 4° C. The volume of the dialysate will be made up to 1 ml and assayed for the enzyme. Ammonium sulfate precipitation is to separate the enzyme from inhibitors. The enzyme activity will be determined at 37° C. in a reaction mixture of 1.0 ml containing 50 mM citrate phosphate buffer (pH 6.0) and 5 μmoles of p-nitrophenyl N-acetyl-α-D-galactosaminide as a substrate. The reaction will be initiated by addition of 100 μl of the dialyzed samples and stopped after 60 min by adding 200 μl of 0.5M $Na_2CO_3$ solution. The reaction mixture will be centrifuged and amount of released p-nitrophenol will be determined by the absorbance of the supernatant at 420 nm and expressed as nmoles/min.

SUMMARY OF THE INVENTION

Cancerous cells and HIV-infected cells secrete α-N-acetylgalactosaminidase into the blood stream, resulting in deglycosylation of serum Gc protein. This inactivates the MAF precursor activity of Gc protein, leading to immunosuppression. Thus, both α-N-acetylgalactosaminidase activity and MAF precursor activity of Gc protein in patient blood stream can serve as diagnostic and prognostic indices.

In one embodiment of the invention, the invention includes a process for determining macrophage activating factor precursor activity in plasma or serum of a person suspected of having cancer or HIV, comprising the step of quantifying in the plasma or serum an amount of vitamin $D_3$-binding protein. The determination of the macrophage activating factor precursor activity provides an indication of the patient's capability to activate its own monocytes/macrophages.

In another embodiment of the invention, the invention includes a process for determining macrophage activating factor precursor activity in plasma or serum of a person suspected of having cancer or HIV comprising the step of quantifying in the plasma or serum an amount of α-N-acetylgalactosaminidase activity. Determining the α-N-acetylgalactosaminidase activity in the plasma or serum provides an indication of a quantity of malignant cells (or HIV-infected cells) in the plasma or serum.

DESCRIPTION OF THE DRAWINGS

Other objects and many attendant features of this invention will become readily appreciated as the same becomes better understood by reference to the following detailed description when considered in connection with the accompanying drawings wherein:

FIG. 1(a) is a schematic illustration of the stepwise generation of macrophage activating factor.

FIG. 1(b) is a schematic illustration of the stepwise deglycosylation of Gc protein.

DETAILED DESCRIPTION OF THE PREFERRED EMBODIMENT

II. Supporting Observations

Mechanisms of macrophage activation by lipid metabolites and a concept developed for therapy of immunodeficient diseases with vitamin D-binding protein derivatives are new and thus far have not been reported in the literature by others. Methods I have developed for diagnostic/prognostic indices are based on the following observations.

A) Cancer Patients

1. Characterization of peripheral blood monocytes/macrophages, lymphocytes and Gc protein in cancer patients.

When peripheral blood monocytes/macrophages (phagocytes) of 175 cancer patients bearing various forms of cancer were treated with a small amount (100 pg/ml) of GcMAF, the phagocytes of all cancer patients were efficiently activated for production of more than 5.0 nmoles of superoxide produced/min/$10^6$ cells, as can be seen at the last column of Table 1. When a mixture of nonadherent (B and T) lymphocytes and monocytes/macrophage (phagocytes) of individual patient was treated with 1 µg lyso-Pc/ml for 30 min and cultured in a medium supplemented with 1 ng Gc protein/ml for 3 hr, the phagocytes of all cancer patients were efficiently activated, indicating that the B and T lymphocytes of all cancer patients are capable of generating macrophage activating factor (MAF) (more than 5.0 nmoles of superoxide produced/min/$10^6$ cells, as can be seen in the 3rd column of Table 1). However, when the lyso-Pc-treated nonadherent and adherent cell mixtures of individual patients were cultured in medium supplemented with patient own plasma (0.1%) for 3 hr, the phagocytes of about ⅓ of the patients were not activated (less than 1.0 nmole of superoxide produced/min/$10^6$ cells, as can be seen at the 2nd column of Table 1). These observations suggest that the patient B and T cells are capable of generating MAF while the MAF precursor activity of Gc protein in the plasma of ⅓ of this patient population was greatly reduced. With this assay procedure, another ⅓ patient population had moderately reduced precursor activity to support macrophage activation for generating 1.5–3.5 nmoles superoxide/min/$10^6$ cells. The remaining cancer patients have precursor activity similar to those of healthy humans. Table 1 is exemplified by the data of the first 13 patients studied. Immunoblotting analysis of cancer patient and healthy human plasma revealed no quantitative change in Gc protein in cancer patients. Thus, lost or reduced precursor activity of Gc protein in certain cancer patients led us to suggest deglycosylation of Gc protein (FIG. 1b). Thus, inflammation-primed macrophage activation can not be developed in certain cancer patients. Since macrophage activation is the first step in the inflammation-primed immune development cascade, these cancer patients are immunosuppressed. This may explain at least in part why cancer patients die after resulted from overwhelming infection.

TABLE 1

Activation of peripheral monocytes/macrophages by treatment with the enzymatically generated macrophage activating factor (GcMAF) or by treatment of mixture of nonadherent (B and T) lymphocytes and adherent cells (monocytes/macrophages) with lysophosphatidylcholine (lyso-Pc) and followed by cultivation in media supplemented with purified Gc protein or plasma protein.

| | | Assay on lyso-Pc | nmoles of superoxide produced/min/$10^6$ cells | | | |
|---|---|---|---|---|---|---|
| Patient No. | Cancer type | +lymphocytes: +phagocytes: Protein: | none phagocytes* none | lymphocytes phagocytes 0.1% plasma | lymphocytes phagocytes 1 ng Gc | none phagocytes* 100 pg GcMAF |
| 1 | Prostate ca.** | | 0.10 | 0.56 | 5.69 | −6.13 |
| 2 | Lung ca. | | 0.14 | 0.89 | 6.36 | 6.97 |
| 3 | Prostate ca. | | 0.05 | 3.96 | 4.86 | 6.20 |
| 4 | Lung ca. | | 0.25 | 0.80 | 5.04 | 5.19 |
| 5 | kidney ca. | | 0.32 | 0.95 | 5.02 | 5.21 |
| 6 | Lung ca. | | 0.21 | 1.99 | 5.32 | 5.82 |
| 7 | Prostate ca. | | 0.29 | 7.44 | 6.73 | 7.47 |
| 8 | Lung small cell ca. | | 0.88 | 1.74 | 6.24 | 6.89 |
| 9 | Lung ca. | | 0.87 | 5.79 | 5.62 | 6.00 |
| 10 | Pharynx/nasal sq. cell ca. | | 1.43 | 6.48 | 7.14 | 8.56 |
| 11 | Cervix squamous cell ca. | | 0.35 | 6.46 | 6.32 | 8.03 |
| 12 | Prostate ca. | | 0.61 | 1.98 | 6.43 | 7.04 |
| 13 | Palate squamous cell ca. | | 0.65 | 5.28 | 6.51 | 10.08 |
| C | Healthy human | | 0.76 | 4.68 | 6.34 | 5.38 |

*phagocytes (monocytes/macrophages) were lyso-Pc-untreated.
**ca., carcinoma. Prostate ca., adenocarcinoma.
The superoxide generating capacity of the phagocytes was expressed as nmoles of cytochrome-c reduced/min/$10^6$ cells.

TABLE 2

N-acetylhexosaminidases detected in cancer patient peripheral blood and lung cancer tissue.

| | N-acetylhexosaminidases[a] | | | | |
|---|---|---|---|---|---|
| Source of Enzyme | Protein[b] (mg) | α-N-acetylgalactosaminidase | | β-N-acetylglucosaminidase | |
| | | total act. (µmoles/hr) | specific act. (µmoles/mg/hr) | total act. (µmoles/hr) | specific act. (µmoles/mg/hr) |
| Normal plasma | 68 | 0.94 | .0138 | 90.37 | 1.329 |
| Patient plasma | 90 | 35.14 | .3901 | 126.63 | 1.407 |
| Lung tumor tissue* | 100 | 192.60 | 1.9260 | 249.04 | 2.490 |

TABLE 2-continued

N-acetylhexosaminidases detected in cancer patient peripheral blood and lung cancer tissue.

| | | N-acetylhexosaminidases[a] | | | |
|---|---|---|---|---|---|
| Source | | α-N-acetylgalactosaminidase | | β-N-acetylglucosaminidase | |
| of Enzyme | Protein[b] (mg) | total act. (μmoles/hr) | specific act. (μmoles/mg/hr) | total act. (μmoles/hr) | specific act. (μmoles/mg/hr) |

[a] α-N-acetylgalactosaminidase and β-N-acetylglucosaminidase activities are expressed as μmoles of nitrophenol production/hour from substrates, p-nitrophenyl N-acetyl-α-D-galactosaminide and p-nitrophenyl N-acetyl-β-D-glucosaminide, respectively.
[b] 70% ammonium sulfate precipitable protein of 1 ml samples of patient no. 1 and healthy human.
*1 g lung cancer tissue was homogenized in 3 ml (15 mM Tris buffer, pH 7).

2. Detection of N-acetylhexosaminidases in cancer patient plasma.

Electrophoretic analysis of patient plasma showed no quantitative change in Gc protein in these patient plasma. Thus, lost or reduced precursor activity of Gc protein in cancer patients suggests deglycosylation of Gc protein. Thus, deglycosylation of Gc protein in plasma may be due to the presence of N-acetylhexosaminidases in the blood stream (FIG. 1b). Patient and healthy human plasma were precipitated with 70% saturated ammonium sulfate. The precipitates were dialyzed and assayed for α-N-acetylgalactosaminidase and β-N-acetylglucosaminidase using p-nitrophenyl N-acetyl-α-D-galactosaminide and p-nitrophenyl N-acetyl-β-D-glucosaminide as substrates. Patients having lost or reduced precursor activity of plasma Gc protein carry a large amount of β-N-acetylglucosaminidase and a significant amount of α-N-acetylgalactosaminidase while about the same amount of β-N-acetylglucosaminidase and extremely low level (1/10) of α-N-acetylgalactosaminidase were found in healthy human plasma (Table 2). Since both healthy human and patient plasma contain the same β-N-acetylglucosaminidase activity level, β-N-acetylglucosaminidase may have nothing to do with deglycosylation of Gc protein. In fact, Gc protein is known to be O-glycosylated (43). When Gc protein as a macromolecular substrate and an equal amount (activity level) of α-N-acetylgalactosaminidase were used, the patient α-N-acetylgalactosaminidase deglycosylated Gc protein while healthy human enzyme was unable to deglycosylate Gc protein as shown in Table 3. This observation led us to conclude that the healthy human enzyme seems to be α-galactosidase simply because α-N-acetylgalactosaminidase and α-galactosidase share the same chromogenic substrate. Thus, α-N-acetylgalactosaminidase was identified in cancer patient blood stream exclusively.

TABLE 3

Macromolecular substrate specificity of α-N-acetylgalactosaminidase activity found in healthy human and cancer patient peripheral blood and lung cancer tissues.
α-N-acetylgalactosaminidase[a]

| Source of Enzyme | Enzyme Amount used total act. (μmoles/hr) | Enzymatically treated Gc protein used for precursor activity assay[b] Superoxide generated (nmoles/min/10^6 cells) |
|---|---|---|
| Normal plasma | 0.24 | 4.09 |
| Patient plasma | 0.26 | 1.31 |
| Lung tumor tissue | 0.24 | 1.33 |
| No enzyme | None | 4.02 |

[a] α-N-acetylgalactosaminidase activity is expressed as μmoles of nitrophenol production/hour from substrate, p-nitrophenyl N-acetyl-α-D-galactosaminide.
[b] After 1 hr incubation of 1 ng Gc protein/ml with the indicated enzyme, the resultant product was added to lyso-Pc-treated mouse peritoneal cells and cultured for 3 hr prior to superoxide generation assay of macrophages.

3. Detection of α-N-acetylgalactosaminidase in cancerous tissues.

Secretion of endo-α-N-acetylgalactosaminidase from tumor tissues is likely to be responsible for deglycosylation of Gc protein in the patient blood stream. Fresh post-operation tumor tissues were obtained and homogenized in 15 mM Tris Buffer at pH 7.0. The homogenates were treated with 70% ammonium sulfate for fractionation and the precipitate was dissolved in 50 mM citrate buffer at pH 4.5 and dialyzed in the same buffer at 4° C. for overnight. Both β-N-acetylglucosaminidase and α-N-acetylgalactosaminidase in tumor tissue homogenate were assayed. As shown in Table 2, large amounts of both β-N-acetylglucosaminidase and α-N-acetylgalactosaminidase were detected in the tumor homogenates (data in Table 2 is exemplified by lung tumor). The latter enzyme was found to deglycosylate Gc protein (Table 3).

It seems likely that secretory capacity of individual tumor tissue for N-acetylgalactosaminidase varies among cancer types. This would result in varying degrees of precursor activity of host plasma Gc protein. The extent of the decreased precursor activity may be reflection of invasiveness of tumor types. Thus, the precursor activity assay of individual patient should have diagnostic/prognostic utilities.

4. Effect of radiation therapy on the precursor activity of Gc protein.

As radiation therapy of cancer patients progressed, the majority of patients who initially had lost or decreased precursor activity of plasma Gc protein had a return toward or to normal (healthy human) values during radiation treatment (see the 2nd column of Table 4). This finding suggests that radiation therapy results in an increase in glycosylated Gc protein in peripheral blood. This also implies that radiation therapy decreases cancer cells capable of secreting α-N-acetylgalactosaminidase. This observation proved the precursor activity of patient Gc protein to be useful diagnostic/prognostic indices.

TABLE 4

Time course study on the precursor activity of Gc protein for the macrophage activating factor in peripheral blood of cancer patients under radiation therapy and activation of peripheral monocytes/macrophages by treatment with GcMAF or by treatment of mixture of lymphocytes (B and T) and monocytes/ macrophages with lysophosphatidylcholine (lyso-Pc) and followed by cultivation in media supplemented with purified Gc protein or 0.1% patient plasma protein.

nmoles of superoxide produced/min/$10^6$ cells

| Patient No. | Day assayed | Treatment*: Protein: | none none | lyso-Pc 0.1% plasma | lyso-Pc 1 ng Gc/ml | none 100 pg GcMAF |
|---|---|---|---|---|---|---|
| 1 | Day 0 | | 0.095 | 0.57 | 5.69 | 6.13 |
|   | Day 7 | | 0.197 | 0.88 | 5.20 | 5.65 |
|   | Day 14 | | 0.382 | 1.94 | 5.81 | 6.41 |
| 2 | Day 0 | | 0.142 | 0.89 | 6.36 | 6.97 |
|   | Day 7 | | 0.497 | 1.90 | 5.98 | 6.45 |
| 3 | Day 0 | | 0.247 | 3.97 | 4.86 | 6.20 |
|   | Day 7 | | 0.284 | 4.42 | 4.90 | 5.66 |
|   | Day 14 | | 0.541 | 6.27 | 6.55 | 8.04 |
| 5 | Day 0 | | 0.323 | 0.95 | 5.04 | 5.21 |
|   | Day 7 | | 0.309 | 0.98 | 5.47 | 5.79 |
|   | Day 14 | | 0.467 | 1.79 | 5.77 | 6.36 |
| 8 | Day 0 | | 0.875 | 1.74 | 6.24 | 6.89 |
|   | Day 7 | | 0.357 | 3.54 | 5.32 | 5.52 |
| 12 | Day 0 | | 0.612 | 1.98 | 6.43 | 7.01 |
|    | Day 7 | | 1.573 | 3.64 | 3.60 | 5.94 |

*Mixture of nonadherent (B and T) cells and adherent (monocytes/macrophages) was treated with 1 μg lyso-Pc/ml for 30 min, washed with PBS and cultured for 3 hr in a medium supplemented with purified Gc protein or 0.1% patient plasma.

5. MAF precursor activity of Gc protein and α-N-acetylgalactosaminidase in oral cancer patient sera.

Among 175 cancer patients, we chose oral cancer patients for prolonged observation because of immediate perceptibility of tumor appearance and metastasis. As shown in Table 5, about ⅓ of total 18 patients exhibited greatly reduced precursor activity of serum Gc protein as expressed by less than 1.2 nmoles of superoxide produced/min/$10^6$ cells. Another ⅓ of this patient population showed moderately reduced precursor activity, ranging for 1.5 to 3.5 nmoles of superoxide produced/min/$10^6$ cells. The remaining patients had precursor activity level equivalent to that of healthy humans.

Since loss of the precursor activity of serum Gc protein is resulted from deglycosylation of Gc protein by α-N-acetylgalactosaminidase, we assayed patient sera for α-N-acetylgalactosaminidase. As shown in Table 5, patients who had very low precursor activities carried very high enzyme activities in their blood stream. Patients who had high precursor activities carried very low enzyme activity. Thus, the enzyme activity levels of all patients showed an excellent inverse correlation with their precursor activity levels as can be seen in Table 5. However, these immunological indices show no correlation with the degree of differentiation of tumors.

About 50% of patients who had low precursor activities (less than 2.25) either were recurrent cases or developed metastasized lymph nodes during 6 month study period. Therefore, precursor activity of Gc protein and α-N-acetylgalactosaminidase activity in patient blood stream were proved to be excellent diagnostic/prognostic indices.

TABLE 5

Histological analysis of squamous cell carcinoma, precursor activities of Gc protein and serum α-N-acetylgalactosaminidase (α-galNAc) of oral cancer patients.

| Patient | | | Precursor activity* | α-galNAc |
|---|---|---|---|---|
| No. | Site | Type | nmoles of superoxide[†] | nmoles/mg/min |
| 1 | Tongue, | Verrucous carcinoma | 2.61 | 1.80 |
| 2 | Tongue, | Well differentiated scc[‡] | 1.94 | 6.51 |
| 3 | Oral floor, | Well differentiated scc. | 5.19 | 1.11 |
| 4 | Upper gingiva, | Moderately differentiated scc. | 4.90 | 1.31 |
| 5 | Oral floor, | Well differentiated scc. | 5.90 | 1.09 |
| 6 | Tongue, | Well differentiated scc. | 4.66 | 1.20 |
| 7 | Lower gingiva, | Well differentiated scc. | 1.07 | 3.51 |
| 8 | Maxillary sinus, | Adenoid cystic carcinoma | 4.23 | 1.22 |
| 9 | Lower gingiva, | Well differentiated scc. | 4.25 | 0.94 |
| 10 | Maxillary sinus, | Poorly differentiated scc. | 2.24 | 2.42 |
| 11 | Tongue, | Well differentiated scc. | 3.45 | 1.96 |
| 12 | Upper gingiva, | Well differentiated scc. | 1.11 | 7.40 |
| 13 | Maxillary sinus, | Poorly differentiated scc. | 2.31 | 3.02 |
| 14 | Buccal mucosa, | Well differentiated scc. | 0.06 | 7.03 |
| 15 | Tongue, | Well differentiated scc. | 1.19 | 7.42 |
| 16 | Lower gingiva, | Well differentiated scc. | 2.14 | 3.12 |
| 17 | Maxillary sinus, | Well differentiated scc. | 0.05 | 7.88 |
| 18 | Lower gingiva, | Well differentiated scc. | 2.76 | 2.34 |
| | Healthy human | | 5.10 | 0.05 |

*Mixture of healthy human lymphocytes (B and T cells) and phagocytes (monocytes/macrophages) cells was treated with 1 μg lyso-Pc/ml for 30 min, washed with PBS and cultured for 3 hr in a medium supplemented with 0.1% patient plasma.
[†]unit is nmoles of cytochrome-c reduced/min/$10^6$ cells.
[‡]scc, squamous cell carcinoma.

B) HIV-infected/AIDS Patients
  1. Characterization of peripheral blood monocytes, macrophages and Gc protein in HIV-infected/AIDS patients.

When peripheral blood monocytes/macrophages (phagocytes) of 65 HIV-infected patients were treated with a small amount (100 pg/ml) of GcMAF, the phagocytes of all patients were activated for generating more than 4.0 nmoles of superoxide produced/min/$10^6$ phagocytes as with healthy humans. When a mixture of lymphocytes and phagocytes of a healthy human was treated with 1 μg lyso-Pc/ml for 30 min and cultured in a medium supplemented with 0.1% patient plasma for 3 h, the phagocytes were not activated with patient plasma of about ⅒ of the total patient population and produced less than 0.7 nmoles of superoxide/min/$10^6$ phagocytes. These patients having severely decreased precursor activity were found to be approximately ¼ of the AIDS patients. The plasma Gc protein of the majority (65%) of HIV-infected patients was capable of being converted to MAF as expressed by more than 4.0 nmoles of superoxide produced/min/$10^6$ phagocytes while the MAF precursor activity of Gc protein in the plasma of approximately 25% of this patient population was moderately reduced (ranging 1.6–3.6 nmoles of superoxide produced/min/$10^6$ phagocytes) as shown in Table 6. This observation suggests that the phagocytes of all HIV-infected patients are capable of being activated while the precursor activity of Gc protein for MAF in the plasma of certain AIDS patients was severely reduced. This may explain at least in part why AIDS patients die from overwhelming bacterial infection.

2. Detection of N-acetylgalactosaminidase in HIV-infected patient plasma.

Electrophoretic analysis of patient plasma showed no quantitative change in Gc protein in these patient plasma. Thus, lost or reduced precursor activity of Gc protein in HIV-infected/AIDS patients suggests deglycosylation of Gc protein. Deglycosylation of Gc protein in plasma was found to be due to the presence of endo-α-N-acetylgalactosaminidase in the patient blood stream. Patients having lost or reduced precursor activity of plasma Gc protein carried significantly large amounts of α-N-acetylgalactosaminidase activity in their blood stream while an extremely low level of α-N-acetylgalactosaminidase activity was detected in healthy human plasma. As shown in Table 7, the enzyme activity in patient plasma showed excellent inverse correlation with the precursor activity of the patient plasma Gc protein, confirming our hypothesis that α-N-acetylgalactosaminidase deglycosylates plasma Gc protein. However, the enzyme activity and CD4$^+$ value of the patients showed no obvious correlation. When Gc protein as a macromolecular substrate was treated with an equal activity (4 nmoles/min) of the enzyme from patient and healthy human plasma, the patient α-N-acetylgalactosaminidase efficiently deglycosylated Gc protein thus inactivated the precursor activity while the healthy human enzyme was unable to deglycosylate Gc protein. The inability of the healthy human enzyme to catabolize Gc protein may imply that this activity in healthy human is α-galactosidase, because α-N-acetylgalactosaminidase and α-galactosidase are evolutionary related, carry 46.9% amino acid sequence homology and share common chromogenic substrate for their catabolic capacities. Thus, a significant amount of α-N-acetylgalactosaminidase was detected exclusively in HIV-infected/AIDS patient blood stream.

TABLE 6

Activation of monocytes/macrophages (phagocytes) and precursor activity of plasma Gc protein of individual HIV-infected/AIDS patients.

| | | nmoles of cytochrome-c reduced/min/$10^6$ cells | | |
|---|---|---|---|---|
| Patient No. | Stage CD4$^{+\S}$ | Assayed on: Protein: | phagocytes* none | phagocytes 100 pg GcMAf | lymphocytes/ phagocytes** 0.1% plasma |

| Patient No. | Stage CD4$^{+\S}$ | phago-cytes* none | phagocytes 100 pg GcMAf | lymphocytes/ phagocytes** 0.1% plasma |
|---|---|---|---|---|
| 1 | 115 | 0.29 | 5.68 | 6.01 |
| 2 | 445 | 0.25 | 4.84 | 4.74 |
| 3 | 516 | 0.67 | 5.12 | 5.39 |
| 4 | 188 | 0.41 | 4.11 | 0.54 |
| 5 | 102 | 0.36 | 4.02 | 3.42 |
| 6 | 136 | 0.67 | 4.04 | 0.69 |
| 7 | 577 | 0.29 | 7.52 | 4.43 |
| 8 | 160 | 0.42 | 4.29 | 5.14 |
| 9 | 222 | 0.87 | 4.21 | 5.22 |
| 10 | 156 | 0.61 | 4.98 | 5.03 |
| 11 | 441 | 0.35 | 4.48 | 4.69 |
| 12 | 298 | 0.10 | 7.22 | 4.52 |
| 13 | 849 | 0.14 | 6.50 | 3.14 |
| 14 | 56 | 0.56 | 5.04 | 4.32 |
| 15 | 22 | 0.84 | 4.32 | 2.91 |
| 16 | 418 | 0.71 | 4.33 | 4.08 |
| 17 | 721 | 0.61 | 4.05 | 4.41 |
| 18 | 989 | 0.44 | 4.26 | 4.04 |
| 19 | 585 | 0.38 | 4.01 | 3.62 |
| 20 | 64 | 0.45 | 4.73 | 4.33 |
| 21 | 845 | 0.08 | 4.85 | 2.91 |
| 22 | 326 | 0.29 | 4.82 | 1.64 |
| 23 | 305 | 0.52 | 4.61 | 4.63 |
| Control† | | 0.54 | 5.01 | 5.10 |

*Phagocytes indicates monocytes/macrophages of patients.
**Precursor activity of plasma Gc protein as measured by superoxide generating capacity of the phagocytes after 3 h incubation of a mixture of lyso-Pc-treated lymphocyte and phagocytes of healthy human with 0.1% plasma of individual patients.
§CD4$^+$ cell count per cubic mm.
† Average of 5 healthy humans.

TABLE 7

α-N-acetylgalactosaminidase activity detected in HIV-infected patient plasma and its correlation with the precursor activity of plasma Gc protein and the CD4$^+$ value of the patients.

| Patient plasma | α-N-acetylgalactosaminidase | Disease stage indices* | |
|---|---|---|---|
| (Patient no.) | Specific activity (nmoles/mg/min) | Precursor act. | CD4$^+$ value |
| Healthy human | 0.056 | 5.12 | ND$^\S$ |
| 4 | 13.12 | 0.54 | 188 |
| 5 | 2.51 | 3.42 | 102 |
| 6 | 12.80 | 0.69 | 136 |
| 7 | 1.13 | 4.43 | 577 |
| 13 | 2.63 | 3.14 | 849 |
| 15 | 3.15 | 2.91 | 22 |
| 19 | 2.28 | 3.62 | 585 |
| 21 | 3.03 | 2.91 | 845 |
| 22 | 3.54 | 1.64 | 326 |

*These values were derived from Table 6.
§Not determined.

References

1. Ngwenya, B. Z., and Yamamoto, N. 1985. Activation of peritoneal macrophages by lysophosphatidylcholine. Biochem. Biophys. Acta 839:9–15.
2. Ngwenya, B. Z. and Yamamoto, N. 1990. Contribution of lysophosphatidyl-choline treated nonadherent cells to mechanism of macrophage stimulation. Proc. Soc. Exp. Biol. Med. 193:118–124.

3. Yagi, F., Eckhardt, A. E. and Goldstein I. J. 1990. Glycosidases of Ehrlich ascites tumor cells and ascitic fluid-purification and substrate specificity inidase and α-galactosidase: comparison with coffee bean α-galactosidase. Arch. Biochem. Biophys. 280:61–67.

4. Yamamoto, N. and Homma, S. 1991. Vitamin $D_3$ binding protein (group-specific component, Gc) is a precursor for the macrophage activating signal from lysophosphatidylcholine-treated lymphocytes. Proc. Natl. Acad. Sci. USA. 88:8539–8543.

5. Yamamoto, N. and Kumashiro, R. 1993. Conversion of vitamin $D_3$ binding protein (Group-specific component) to a macrophage activating factor by stepwise action of β-galactosidase of B cells and sialidase of T cells. J. Immunol. 151:2794–2902.

6. Homma, S., Yamamoto, M. and Yamamoto, N. 1993. Vitamin D binding protein (group-specific component, Gc) is the sole serum protein required for macrophage activation after treatment of peritoneal cells with lysophosphatidylcholine. Immunol. Cell Biol. 71:249–257.

7. Yamamoto, N., Kumashiro, R., Yamamoto, M., Willett, N. P. and Lindsay, D. D. 1993. Regulation of inflammation-primed activation of macrophages by two serum factors, vitamin $D_3$-binding protein and albumin. Inf. Imm. 61:5388–5391.

8. Yamamoto, N., Willett, N. P. and Lindsay, D. D. 1994. Participation of serum proteins in the inflammation-primed activation of macrophages. Inflammation. 18:311–322.

9. Naraparaju, V. R. and Yamamoto, N. 1994. Roles of β-galactosidase of B lymphocytes and sialidase of T lymphocytes in inflammation-primed activation of macrophages. *Immunol. Lett.* 43:143–148.

Without further elaboration the foregoing will so fully illustrate my invention that others may, by applying current or future knowledge, adapt the same for use under various conditions of service.

I claim:

1. A process for determining α-N-acetylgalactosaminidase activity in plasma or serum of a patient suspected of containing human immunodeficiency virus comprising the steps of precipitating the plasma or serum containing α-N-acetylgalactosaminidase activity to produce a precipitate, dialyzing the precipitate and then incubating the precipitate with p-nitrophenyl-N-acetyl-α-D-galactosaminide.

2. The process of claim 1 wherein the precipitate is produced by the step of subjecting the plasma or serum to ammonium sulfate.

3. The process of claim 1 wherein the step of dialyzing the precipitate includes the step of dialyzing the precipitate in a phosphate buffer.

4. A process for determining α-N-acetylgalactosaminidase activity in plasma or serum of a patient suspected of having cancer comprising the steps of precipitating the plasma or serum containing α-N-acetylgalactosaminidase activity to produce a precipitate, dialyzing the precipitate and then incubating the precipitate with p-nitrophenyl-N-acetyl-α-D-galactosaminide.

5. The process of claim 4 wherein the precipitate is produced by the step of subjecting the plasma or serum to ammonium sulfate.

6. The process of claim 4 wherein the step of dialyzing the precipitate includes the step of dialyzing the precipitate in a phosphate buffer.

\* \* \* \* \*